United States Patent
Agnello et al.

(10) Patent No.: US 12,257,021 B2
(45) Date of Patent: Mar. 25, 2025

(54) DYNAMICALLY ADJUSTABLE FRAME RATE FROM MEDICAL DEVICE CONTROLLER

(71) Applicant: Abiomed, Inc., Danvers, MA (US)

(72) Inventors: Alessandro Simone Agnello, Peabody, MA (US); Victor Medina, Lynn, MA (US); Robert Lussier, Methuen, MA (US); Paul Roland Lemay, Nashua, NH (US)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 16/365,293

(22) Filed: Mar. 26, 2019

(65) Prior Publication Data
US 2020/0314207 A1 Oct. 1, 2020

(51) Int. Cl.
*A61B 5/00* (2006.01)
*G16H 30/40* (2018.01)
(Continued)

(52) U.S. Cl.
CPC .......... *A61B 5/0013* (2013.01); *G16H 30/40* (2018.01); *G16H 40/67* (2018.01); *H04L 67/125* (2013.01); *H04L 67/61* (2022.05)

(58) Field of Classification Search
CPC ...... A61B 5/0013; G16H 30/40; G16H 40/67; H04L 67/61; H04L 67/125
See application file for complete search history.

(56) References Cited

U.S. PATENT DOCUMENTS 7,580,755 B1 * 8/2009 Schwartz ........... A61N 1/37282
128/903
10,130,256 B2 * 11/2018 Berger .................... A61B 5/742
(Continued)

FOREIGN PATENT DOCUMENTS

CN 101790034 A 7/2010
CN 103946885 A 7/2014
(Continued)

OTHER PUBLICATIONS

"Welch Allyn 1500 Patient Monitor User Manual", Hillrom website, Dec. 31, 2011 [retrieved on Oct. 23, 2021]. (Year: 2011).*
(Continued)

*Primary Examiner* — Thomas J Dailey
(74) *Attorney, Agent, or Firm* — BOTOS CHURCHILL IP LAW LLP

(57) ABSTRACT

A medical device monitoring system and method extract information from screen images from medical device controllers, and intelligently vary rates at which the screen images are fetched from the respective medical device controllers, so as to reduce computer network load, timely report high-priority information, such as alarms, and provide information at intervals requested by users. The rates at which the screen images are fetched are automatically varied based on information available to a server, such as available network bandwidth, level of network congestion, number of medical device controllers co-located at a single medical institution or on a given local area network (LAN), alarm status of a medical device controller and/or historical timing information regarding use of medical devices connected to the medical device controllers.

25 Claims, 5 Drawing Sheets

(51) Int. Cl.
  *G16H 40/67* (2018.01)
  *H04L 67/125* (2022.01)
  *H04L 67/61* (2022.01)

(56) References Cited

U.S. PATENT DOCUMENTS

| | | | |
|---|---|---|---|
| 10,206,570 B2* | 2/2019 | McKenna | A61B 5/0002 |
| 10,325,472 B1* | 6/2019 | Harsdorff | A61B 5/1117 |
| 2002/0169583 A1 | 11/2002 | Gutta et al. | |
| 2008/0021730 A1* | 1/2008 | Holla | G16H 40/67 |
| | | | 705/2 |
| 2009/0192813 A1 | 7/2009 | Gejdos et al. | |
| 2010/0017233 A1 | 1/2010 | Toda | |
| 2010/0056875 A1* | 3/2010 | Schoenberg | A61B 5/0002 |
| | | | 600/300 |
| 2011/0034783 A1* | 2/2011 | Lisogurski | A61B 5/0002 |
| | | | 600/301 |
| 2011/0212216 A1 | 9/2011 | Carlson et al. | |
| 2012/0330680 A1 | 12/2012 | O'Larte | |
| 2014/0073860 A1* | 3/2014 | Urtti | A61B 5/746 |
| | | | 600/300 |
| 2014/0098209 A1* | 4/2014 | Neff | A61B 5/742 |
| | | | 348/77 |
| 2014/0222805 A1* | 8/2014 | Huang | G06F 16/90335 |
| | | | 707/732 |
| 2014/0233788 A1* | 8/2014 | Fox | G06K 9/64 |
| | | | 382/103 |
| 2014/0235975 A1* | 8/2014 | Carnes | G16H 40/67 |
| | | | 600/323 |
| 2015/0016283 A1* | 1/2015 | Lyle | H04L 67/1029 |
| | | | 370/252 |
| 2015/0049947 A1* | 2/2015 | Katsaros | G06K 9/00979 |
| | | | 382/182 |
| 2015/0220814 A1* | 8/2015 | Verkasalo | G06Q 30/0242 |
| | | | 382/103 |
| 2016/0356880 A1 | 12/2016 | Negussu et al. | |
| 2017/0011200 A1 | 1/2017 | Arshad et al. | |
| 2017/0193322 A1* | 7/2017 | Schiller | A61B 5/0077 |
| 2017/0195202 A1 | 7/2017 | Yamasaki et al. | |
| 2018/0078159 A1* | 3/2018 | Edelman | A61M 60/221 |
| 2018/0122518 A1* | 5/2018 | Choudhary | G06F 19/3418 |
| 2018/0153753 A1* | 6/2018 | Kostic | A61G 7/0527 |
| 2018/0343596 A1* | 11/2018 | Soro | A61B 5/14551 |
| 2018/0374568 A1 | 12/2018 | Agnello | |
| 2019/0074089 A1* | 3/2019 | Kochura | G16H 50/30 |
| 2019/0290215 A1* | 9/2019 | Gilbert | A61B 1/04 |

FOREIGN PATENT DOCUMENTS

| | | |
|---|---|---|
| WO | 2017164879 A1 | 9/2017 |
| WO | 2017164897 A1 | 9/2017 |

OTHER PUBLICATIONS

Retrieved from the Internet: <URL: https://www.hillrom.com/content/dam/hillrom-aem/us/en/marketing/products/1500-patient-monitor/documents/1500%20Patient%20Monitor%20Software%20version%201.3.X, (Year: 2011).*

Bent et al. "Optimizing sampling rate of wrist-worn optical sensors for physiologic monitoring", Journal of Clinical and Translational Science 5: e34, pp. 1-8, Aug. 14, 2020. DOI: 10.1017/cts.2020.526. (Year: 2020).*

Mahmud et al., "Cloud-Fog Interoperability in IoT-enabled Healthcare Solutions", ICDN '18 Proceedings of the 19th International Conference on Distributed Computing and Networking; Varnasi, India, Jan. 4-7, 2018, 10 pages.

International Searching Authority, International Search Report—International Application No. PCT/US2020/024571 dated Jun. 8, 2020, together with the Written Opinion of the International Searching Authority, 16 pages.

Office Action from corresponding Indian Patent Application No. 202117044528 dated Jan. 15, 2024 (6 pp.).

Office Action from corresponding Israeli Patent Application No. 286632 dated Dec. 24, 2023 (4 pp.).

Office Action issued in Chinese Patent Application No. 2020800239001 dated Sep. 26, 2023 (23 pp.).

Office Action dated Apr. 19, 2024 in Japanese Patent Application No. 2021-557336 (8 pp.).

Office Action from corresponding Israeli Patent Application No. 286632 dated Aug. 26, 2024 (3 pp.).

Examination Report No. 1 in corresponding AU Application No. 2020248394, issued Oct. 14, 2024. 2 pages.

* cited by examiner

DYNAMICALLY ADJUSTABLE FRAME RATE FROM MEDICAL DEVICE CONTROLLER

BACKGROUND

Technical Field

The present invention relates to remotely monitoring medical devices and, more particularly, to dynamically adjusting a frame rate at which images of screens displayed by medical device controllers are requested for optical character recognition (OCR) processing of the images.

RELATED ART

Many medical devices, such as some intravascular blood pumps, for example the Impella® 2.5 heart pump available from Abiomed, Inc., Danvers, Mass., are connected to external medical device controllers that collect and display operational data about the medical devices, such as heart signal level, battery temperature, blood flow rate and plumbing integrity. An exemplary medical device controller is available from Abiomed, Inc. under the trade name Automated Impella Controller®. The medical device controllers raise alarms when operational data values fall beyond predetermined values or ranges, for example if a leak or loss of suction is detected. These medical device controllers include video display screens as human interfaces, on which the operational data and/or alarms are displayed.

To facilitate remote monitoring by medical personnel to ensure efficacy and patient safety, some such medical device controllers may be coupled via computer networks, often including wireless segments, to central servers, which may be accessed by monitoring stations. The monitoring stations may display real-time operational data and/or alarms on display screens for viewing by the medical personnel.

The servers request and receive images of contents displayed on the screens of the medical device controllers. Some servers use optical character recognition (OCR) technology to parse the images and extract textual information, such as heart pump serial number, blood flow rate, warning message text and the like.

However, network congestion and intermittent wireless network connectivity make it difficult or impossible for the servers to fetch the images from the medical device controllers in a timely fashion, possibly leading to missed or delayed notifications of alarms and the like. Furthermore, each OCR request issued by the servers incurs a cost. This cost creates a tension between low-cost operation (infrequent image analysis, at the risk of delayed information reporting) and low-latency information reporting (frequent image analysis).

SUMMARY OF EMBODIMENTS

An embodiment of the present invention provides a medical device monitoring system. The medical device monitoring system includes a server. The server is configured to automatically request and receive images. The server is configured to request and receive the images via a computer network from each medical device controller of a plurality of medical device controllers. Each image includes contents displayed on a screen of a medical device controller. The server is also configured to have at least a portion of each image optical-character-recognized. The server is further configured to dynamically adjust a rate at which the server requests the images from each medical device controller.

In any embodiment, the server may be configured to dynamically adjust the rate based on information about the medical device controller.

In any embodiment, the information about the medical device controller may be provided by the medical device controller.

In any embodiment, the information about the medical device controller may include information about an alarm state of the medical device controller.

In any embodiment, the information about the medical device controller may include information about an operational parameter.

In any embodiment, the information about the medical device controller may include information about a power source for the medical device controller.

In any embodiment, the information about the medical device controller may include information about a number of users simultaneously monitoring the medical device controller.

In any embodiment, the server may be configured to dynamically adjust the rate based on information about the computer network.

In any embodiment, the information about the computer network may include information about a load on the computer network.

In any embodiment, the information about the computer network may include historical information about reliability of the computer network.

In any embodiment, the information about the computer network may include information about signal strength of a wireless network connection available to the medical device controller.

In any embodiment, the information about the computer network may include information about a number of other medical device controllers co-located with the medical device controller at a facility.

In any embodiment, the server may be configured to dynamically adjust the rate based on information about workload on the server.

In any embodiment, the server may be configured to dynamically adjust the rate based on input from a human user.

In any embodiment, the server may be configured to dynamically adjust the rate based on historical information.

In any embodiment, the historical information may include historical information about timing of connection of a medical device to the medical device controller.

In any embodiment, the historical information may include historical information about accuracy of the optical-character-recognition of at least one earlier image.

In any embodiment, the server may be further configured to dynamically adjust a number of servers that request optical character recognition of the at least the portion of each image. Another embodiment of the present invention provides a method of monitoring a medical device. The method includes automatically requesting and receiving images of contents displayed on a screen of a medical device controller. The images are requested and received via a computer network. The images are requested and received from each medical device controller of a plurality of medical device controllers. The method also includes automatically having at least a portion of each image optical-character-recognized, and automatically dynamically adjusting a rate at which the images are requested.

In any embodiment, information about the medical device controller may be received. Automatically dynamically adjusting the rate at which the images are requested may involve automatically dynamically adjusting the rate based on the information about the medical device controller.

In any embodiment, information about the computer network may be received. Automatically dynamically adjusting the rate at which the images are requested may involve automatically dynamically adjusting the rate based on the information about the computer network.

In any embodiment, information about workload on a server may be received. Automatically dynamically adjusting the rate at which the images are requested may involve automatically dynamically adjusting the rate based on the information about the workload on the server.

In any embodiment, an input from a human user may be received. Automatically dynamically adjusting the rate at which the images are requested may involve automatically dynamically adjusting the rate based on the input from the human user.

Yet another embodiment of the present invention provides a non-transitory computer-readable medium. The medium is encoded with instructions. When executed by a processor, the instructions establish processes for performing a computer-implemented method of monitoring a medical device. The processes include a process configured to automatically request and receive images of contents displayed on a screen of a medical device controller. The images are requested and received via a computer network from each medical device controller of a plurality of medical device controllers. A process is configured to automatically have at least a portion of each image optical-character-recognized. A process is configured to automatically dynamically adjust a rate at which the images are requested.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Embodiments of the present invention provide a medical device monitoring system and method that extract information from screen images from medical device controllers, and intelligently vary rates at which the screen images are fetched from the respective medical device controllers, so as to reduce computer network load, timely report high-priority information, such as alarms, and provide information at intervals requested by users. The rates at which the screen images are fetched are automatically varied based on information available to a server, such as available network bandwidth, level of network congestion, number of medical device controllers co-located at a single medical institution or on a given local area network (LAN), alarm status of a medical device controller and/or historical timing information regarding use of medical devices connected to the medical device controllers.

Figure 1:
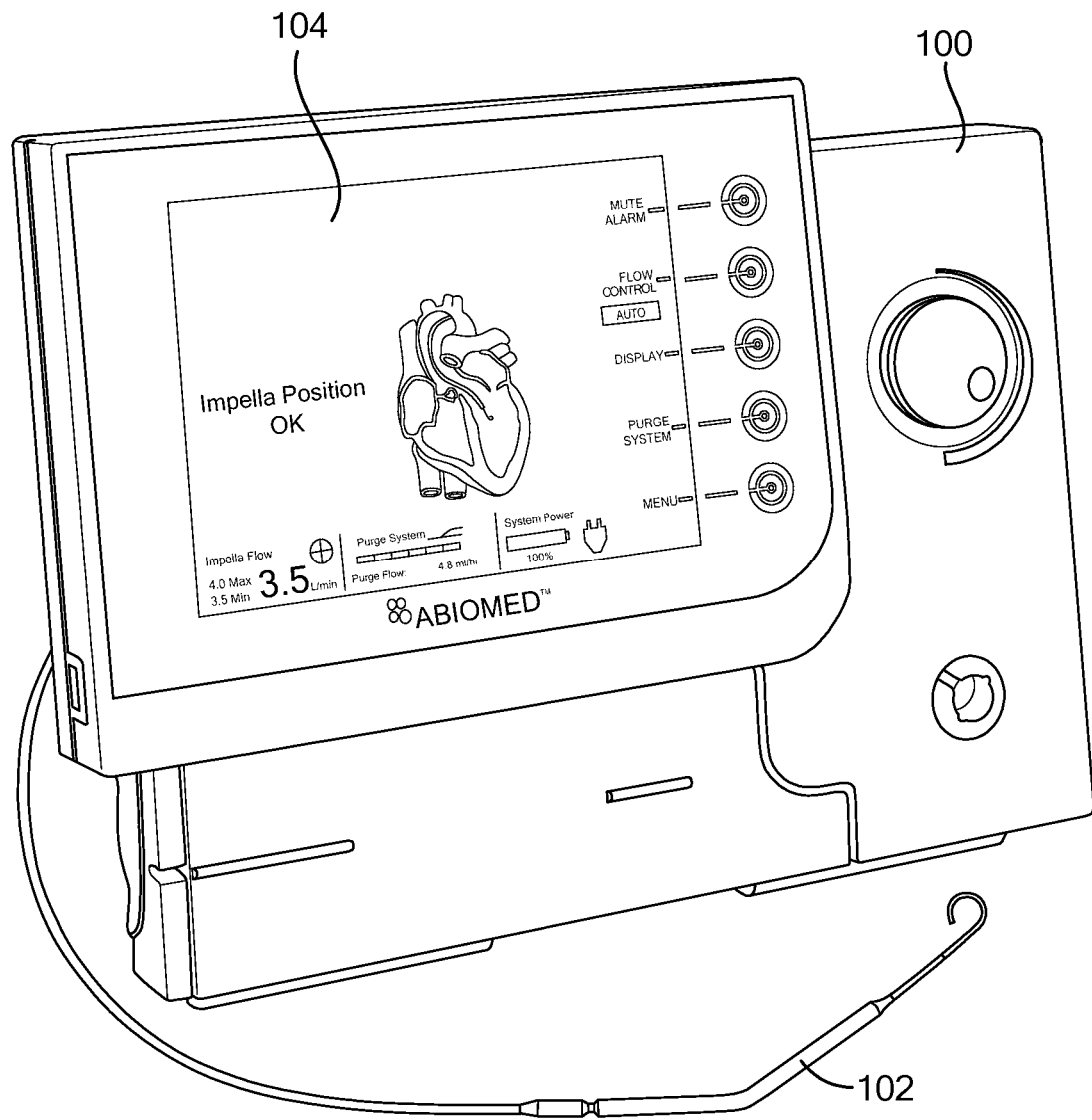
FIG. 1 is a perspective view of an exemplary convention medical device controller and an exemplary conventional medical device, in this example a heart pump, coupled to the medical device controller, according to the prior art.

FIG. 1 is a perspective view of an exemplary convention medical device controller 100 and an exemplary conventional medical device 102, in this example a heart pump, coupled to the medical device controller 100. In the example shown in FIG. 1, the medical device controller 100 is an Automated Impella Controller® from Abiomed, Inc., Danvers, Mass., and the heart pump 102 is an Impella® 2.5 heart pump, also available from Abiomed, Inc., although any suitable medical device controller may be used. In some cases, the medical device and its associated medical device controller are combined. Such a combination is referred to herein simply as a medical device controller.

The medical device controller 100 includes a display screen 104, on which the medical device controller 100 displays operational data about the medical device 102, such as heart signal level, battery temperature, blood flow rate and plumbing integrity. As discussed in more detail herein, the medical device controller 100 may be connected to a computer network and thereby send images of contents displayed on the screen 104 to a remote server (not shown).

Figure 2:
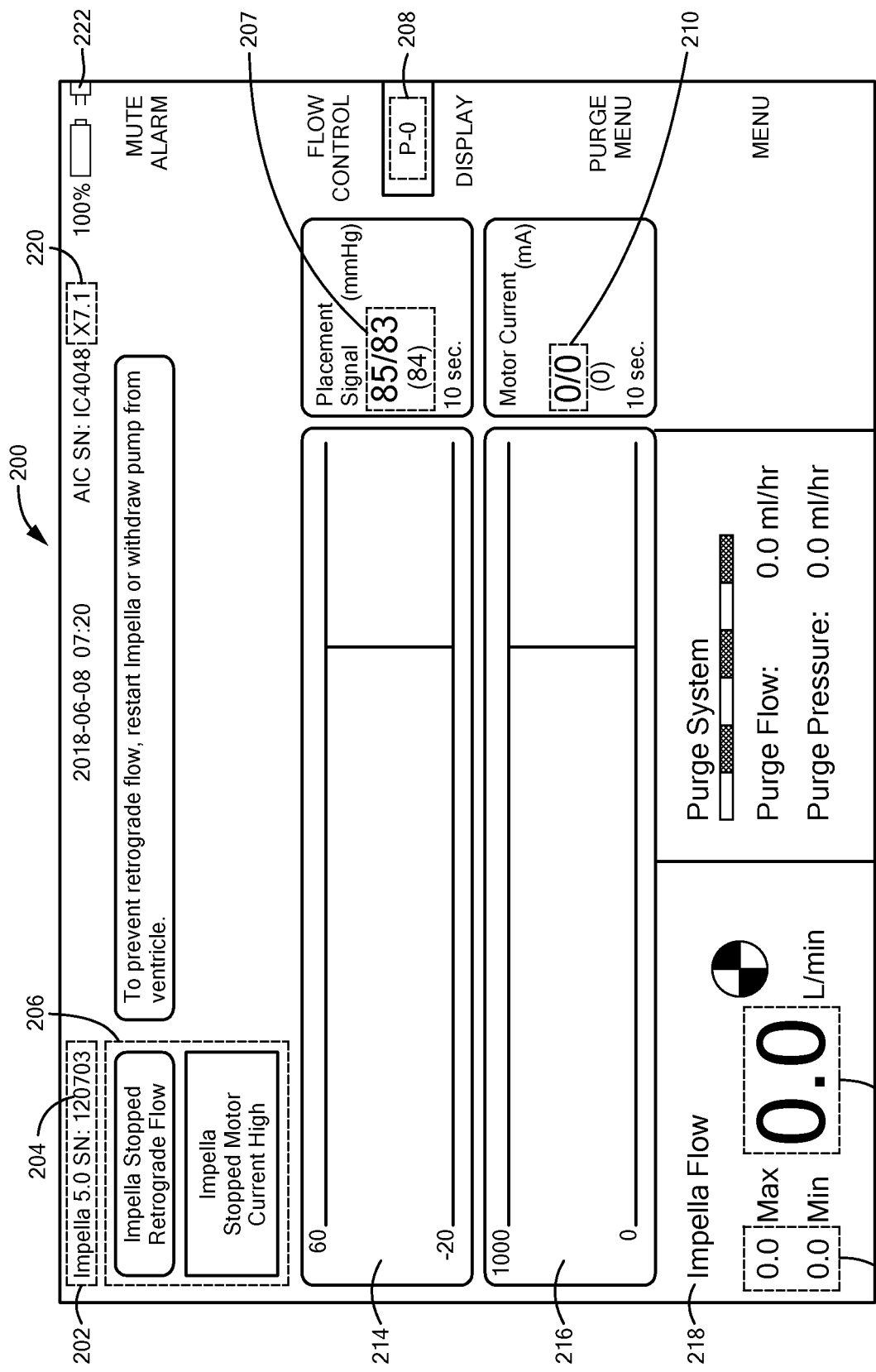
FIG. 2 shows exemplary hypothetical display screen contents that may be displayed on a screen of the medical device controller of FIG. 1, according to the prior art.

FIG. 2 shows exemplary hypothetical display screen contents 200 that may be displayed on the screen 104 of the medical device controller 100 of FIG. 1. For example, the display screen contents may include a heart pump type ("Impella 5.0") 202, a heart pump serial number ("120703") 204, a warning/error message 206, a placement signal 207, a present heart pump speed (performance) setting ("P-0") 208, a heart pump motor current value 210, a current or average blood flow rate 212 and minimum and maximum blood flow rates 213. The display screen contents 200 are typically pixelated.

Figure 3:
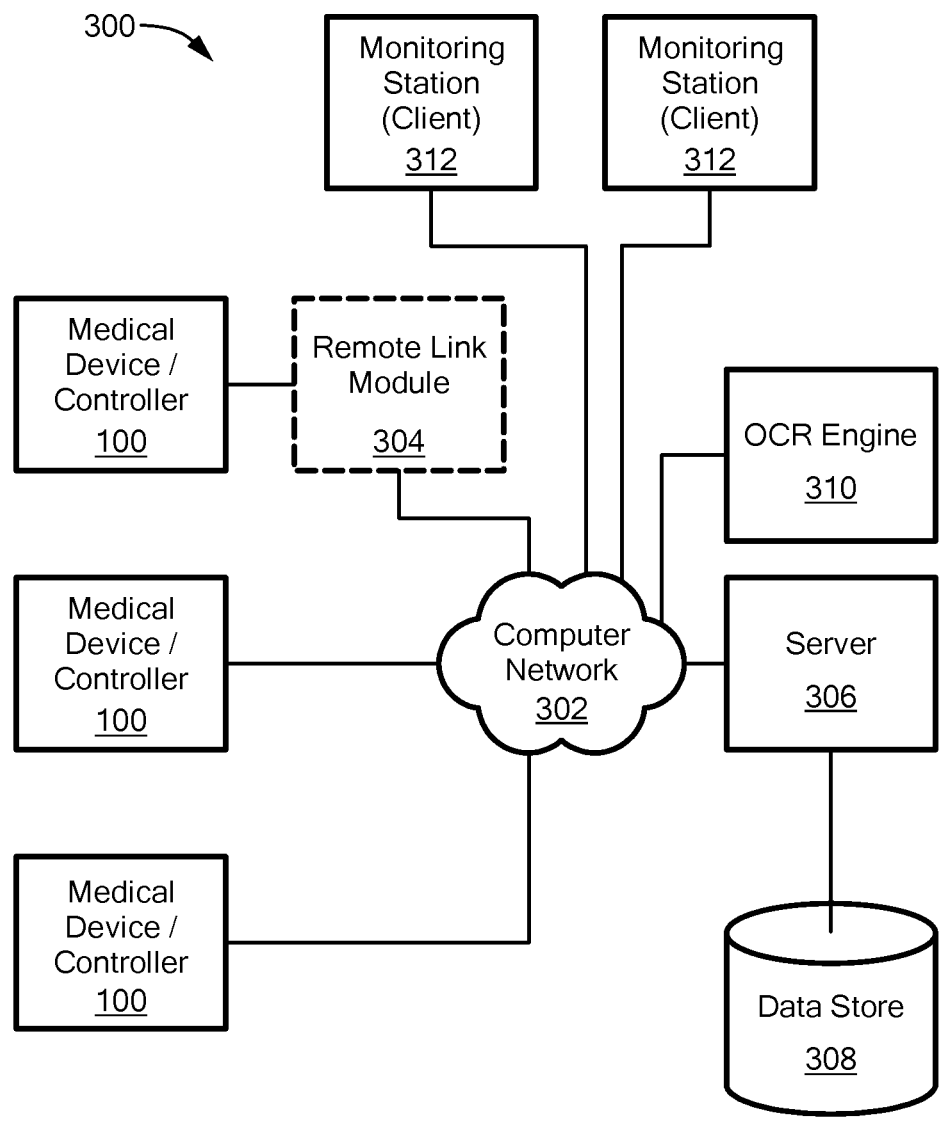
FIG. 3 is a schematic block diagram of major components of a medical device monitoring system for collecting, storing and retrieving operational data from and about a plurality of medical device controllers, such as the medical device controller of FIGS. 1 and 2, according to an embodiment of the present invention.

FIG. 3 is a schematic block diagram of major components of a medical device monitoring system 300 for collecting, storing and retrieving operational data from and about a plurality of medical device controllers 100. For simplicity, only medical device controllers 100, and not separate medical devices, are shown in FIG. 3. Although three medical device controllers 100 are shown, other numbers of medical device controllers 100 may be used. Each medical device controller 100 is connectable to a computer network 302, optionally via a remote link module 304. Each medical device controller 100 is configured to automatically repeatedly capture status information about the medical device connected thereto and display the status information on a display screen 104 (FIG. 1). As noted, FIG. 2 shows respective hypothetical display screen contents 200 that may be displayed on the screen 104 of any given medical device controller 100.

A server 306 is configured to automatically periodically or occasionally request and receive an image of the contents displayed on the screen 104 of each medical device controller 100, typically about every 20 second. The request and the image are sent via the computer network 302. The image may be sent in one or more messages encoded as a video frame or a sequence of video frames. The video frame(s) may, for example, contain pixelated copies of images displayed on the display screens 104 of the medical device controllers 100.

The server 306 is configured to process the received frames (images). As noted, the server 306 parses the images and extracts textual information, such as heart pump serial number, blood flow rate, warning message text and the like, by optical character recognizing (OCR) portions of the images. The server 306 may also parse the images and extract graphical information, such as a power source icon, and compare this graphical information to predetermined pixel patterns and/or colors. The server 306 may include an OCR engine, or the server 306 may communicate with an external OCR engine 310, such as via the computer network 302. The server 306 may then use the recognized text to automatically ascertain serial numbers or other identifiers of the medical device controllers 100, operating parameters of the medical device controllers 100, whether an alarm has been raised by one of the medical device controllers 100, etc.

A data store 308 is configured to store one or more media files, and in particular frames (images), such as MP4 video or other suitable types of media files, and the server 306 is configured to automatically store received frames (images) in the data store 308. The data store 308 records the screen images received by the server 306 for later playback, such as in response to requests from one of several monitoring stations 312. The monitoring stations 312 may use cloud-based technology to securely and remotely display images of the medical device controller 100 screens 104 to physicians and hospital staff anywhere with Internet connectivity. An exemplary remote monitoring system is available under the trade name Impella Connect® online device management system, available from Abiomed, Inc., Danvers, Mass.

The data store 308 is configured to provide a requested portion of the stored media file in response to a provision request. The data store 308 thereby supports playback of the medical device controller 100 status information. For example, the data store 308 may provide one or more frames (images) of video stored in the media file, for display to a user. The server 306 may also be configured to provide status information about one or more of the medical device controllers 100 to ones of the monitoring stations 312, based on images received by the server 306 in real time and/or based on historical information held in the data store 308.

However, congestion in the computer network 302, such as congestion in computer networks internal to medical institutions, and unreliable wireless network connections, create a challenging environment for the server 306 to request and timely receive the images from the medical device controllers 100. Furthermore, each image is separately processed by the OCR engine 310, and each OCR request issued by the server 306 incurs a cost.

Embodiments of the present invention solve these problems by automatically dynamically adjusting a rate at which the server 306 requests the images from the medical device controllers 100. Optionally or alternatively, the server 306 sends a (possibly different) rate to each medical device controller 100, and in response each medical device controller 100 sends its images to the server 306 at the commanded rate, without an explicit request from the server 306 for each image. For simplicity of explanation, here and in the claims, dynamically adjusting a rate at which the server 306 "requests the images" encompasses both: (a) the server 306 explicitly requesting each image and (b) the server 306 commanding a rate at which a medical device controller 100 should send images, without an explicit request for each image.

The server 306 may request the images at different rates from different ones of the medical device controllers 100, and the server 306 may dynamically adjust the rates independently for different ones of the medical device controllers 100. Exemplary factors used by the server 306 to automatically determine an image rate from a particular medical device controller 100, or group of medical device controllers 100, include: level of network congestion, whether a medical device controller 100 is alarming, alarm severity, whether a heart pump 102 or other medical device is connected to a particular medical device controller 100, patient condition and user command.

The server 306 may automatically dynamically adjust the rates at which the images are requested, based on information in a variety of categories, such as: (a) information from the medical device controller 100, (b) information about the computer network 302, (c) information about the server 306 or other servers, such as the OCR engine 310, and (d) information from or about a human user of the system 300 or a patient. Some of the information in any of the categories may be historic. Examples from each of these categories are provided below. Different and/or other categories of information may be used as needed to meet or approach operational objectives.

Figure 4:
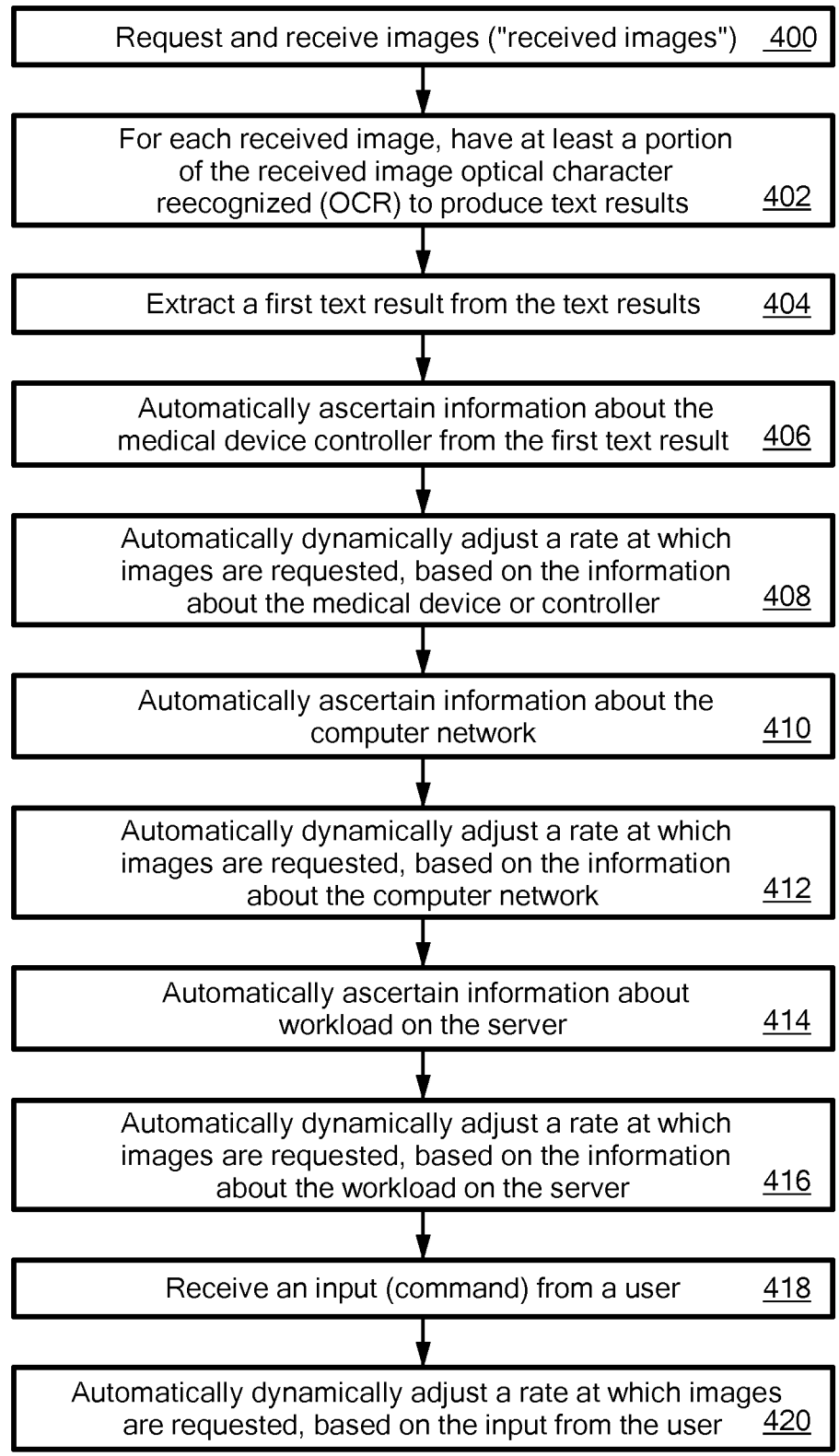
FIG. 4 is a flowchart schematically illustrating a method of monitoring a medical device, such as a method performed by a server of FIG. 3, according to an embodiment of the present invention.

FIG. 4 is a flowchart schematically illustrating a method of monitoring a medical device 100. The server 306 (FIG. 3) may perform this method. At operation 400, the method requests and receives images ("received images"). The received images are requested and received via the computer network 302. The received images are requested and received from each medical device controller 100 of a plurality of medical device controllers. Each received image includes contents displayed on a screen 104 of the medical device controller 100.

At 402, for each received image, at least a portion of the image is optical-character-recognized via a service call to the OCR engine 310 to produce text results. At 404, a first text result is extracted from the text results. The first text result is extracted from a portion of the image that contains information about the medical device controller 100 and/or a medical device, such as a heart pump, connected to the medical device controller 100. At 406, information about the medical device controller 100 is automatically ascertained from the first text result.

Optionally or alternatively, one or more portions of the received image may be analyzed, such as by comparing the portions on a per-pixel basis to a set of predetermined pixel patterns and/or predetermined colors, to automatically determine information about the medical device controller 100 and/or a medical device connected to the medical device controller 100. For example, a power source icon 222 in the image may be compared to a predetermined pattern to automatically determine whether the medical device controller 100 is currently powered by a battery or by mains.

At 408, the rate at which images are requested from the medical device controller 100 is automatically dynamically adjusted, based on the information about the medical device controller 100 or the associated medical device 102. "Dynamically" means the rate is changed over time, not only once. The rate may be changed as frequently as the server 306 detects reasons to change the rate, or less frequently.

Examples of the first category of information, i.e., information received from the medical device controller 100, that may be automatically ascertained from the image, and how this information influences the image request rate, are listed in Table 1. For example, if OCR of the current image from a medical device controller 100 fails, the server 306 may change the interval to zero, so as to immediately request a new image, at least until an image is, or a predetermined number (such as three) of successive images are, successfully OCR processes, after which the interval may be returned to a default value, or a value determined by other information. If, however, a predetermined number of successive images incur OCR failures, the server 306 should increase the interval and raise an error.

The server 306 receives information from the medical device controllers 100 when significant events occur, such as when a medical device controllers 100 power on and when a heart pump 102 is connected to a medical device controller 100. The server 306 may be configured to store information, such as time, of these events. The server 306 may be further configured to calculate statistics and store statistical or historical information, such as a calculated average amount of time between when a medical device controller 100 is powered on and when a heart pump 102 or other medical device is connected to the medical device controller 100. After a statistically significant number of samples have been collected by the server 306, upon detecting that a medical device controller 100 has powered on, the server 306 can set the image request interval to a relatively high value, such as about 1 minute, for about 70% of the average time until a heart pump 104 is connected, and thereafter automatically switch to the default interval, such as about 20 seconds, or another predetermined value.

The examples in Table 1 relate to a particular type of medical device controller 100 and a particular type of medical device (a heart pump). Other types of medical device controllers and medical devices may provide different types of information and thus may have different types of triggers and different intervals. Thus, the contents of Table 1 should not be viewed as a limitation on the breadth of this disclosure or the appended claims. The same applies to other tables included herein.

TABLE 1

Exemplary information about a medical device controller

| Name | Trigger | Interval |
| --- | --- | --- |
| Alarm text 206 | "Impella Stopped" | 3 sec. |
| Alarm text 206 | "Air in Purge System" | 10 sec. |
| Alarm text background color | Yellow | 10 sec. |
| Alarm text background color | Red | 5 sec. |
| Placement signal 207 | >100 | 15 sec. |
| Motor current 210 | <0.1 OR >5 | 10 sec. |
| Avg. blood flow rate 212 | <1 OR >8 | 5 sec. |
| Min. blood flow rate 213 | <1 | 3 sec. |
| Max. blood flow rate 213 | >8 | 3 sec. |
| Connected blood pump 202 | (none) | 1 min. |
| Connected blood pump 202 | (any) | 20 sec. |
| Power source icon 222 | Battery | 1 min. |
| Power source icon 222 | Mains | 20 sec. |
| OCR failure on current image | TRUE | 0 sec. |
| Any field validation failure | TRUE | 5 sec., until valid |

The server 306 is configured to automatically dynamically adjust the rate that images are requested from the medical device controller 100, based on information about the medical device controller 100. Each entry in Table 1 includes a name of a piece of information, a trigger condition and an interval. If the server 306 detects a condition in the information that meets the trigger condition of an entry in Table 1, the server 306 may change the interval at which the server 306 requests images from the corresponding medical device controller 100 to the interval value in the table entry. The server 306 may use additional rules to control to what value the image request interval is changed and/or how frequently the image request interval is changed. If multiple conditions are met, the server 306 may change the image request interval to the shortest interval of the met conditions, or to the longest interval of the met conditions, based on additional rules.

If no condition in the table is met, the server 306 may revert to a default interval, such as about 20 seconds. Some of the conditions may cause a change in the image request interval to a value larger than the default value. For example, if no blood pump is currently connected to a given medical device controller 100, the image request interval may be made relatively large, because the medical device controller 100 is essentially not currently in use, and it therefore currently provides no particularly useful information. On the other hand, for example, if the alarm text 206 indicates a problem, the image request interval may be made relatively small, to cause displays on the monitoring station(s) 312 to be refreshed more frequently, so personnel observing the monitoring station(s) 312 receive more current information.

Optionally, the server 306 may perform validation tests on the text results returned by the OCR engine 310. For example, if a field, such as average blood flow rate 212 (FIG. 2) is expected to be numeric, the returned OCR text may be checked and accepted only if it contains only numeric characters, and an optional decimal point. Numeric fields may be range checked. For example, if it is known a priori that each placement signal 207 value must be in a range 0-100, the returned OCR text may be compared to this range. If a field fails its respective validation test, the interval may be reduced, for example to 5 seconds, until an image is OCR processed to yield a valid value for the field.

Although the examples in Table 1 are simple conditions, the server 306 may use combinations of conditions to automatically determine the image request interval. For example, if the average blood flow rate 212 is less than 1 or greater than 8, and the minimum blood flow rate 213 is less than 1, the server 306 may change the image request interval to 1 second, i.e., less than the interval for either of the two conditions separately.

Other examples of the first category of information, i.e., information received from the medical device controller 100, include any information that is available in the image, such as: pump performance level 208, any specific alarm 206, local time 224 and pump serial number 204. The pump performance level 208 is an indication of an operational parameter, in this case essentially desired pump speed, set by a user of the medical device controller 100, such as through a user interface implemented using the display screen 104 on the medical device controller 100.

Figure 5:
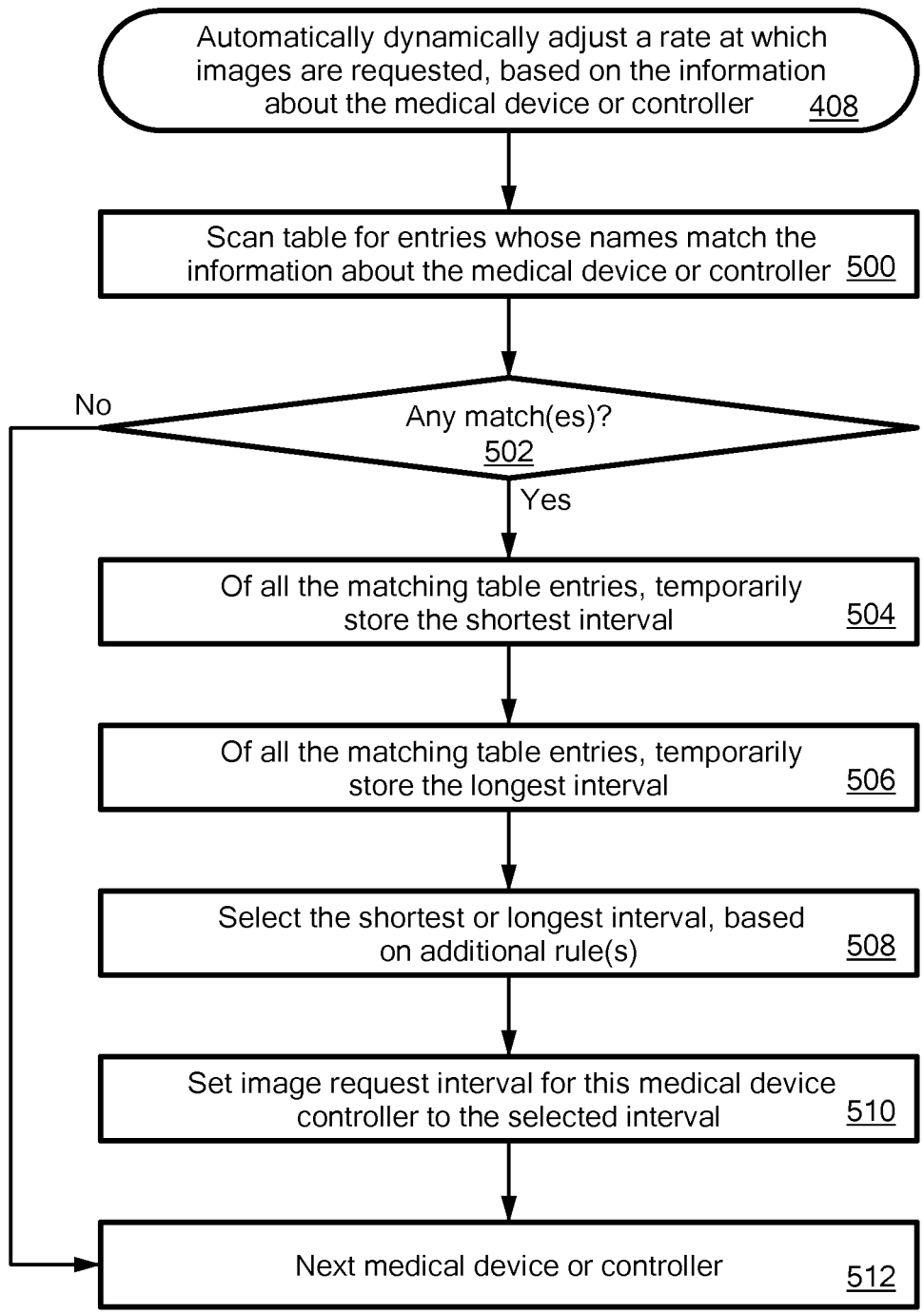
FIG. 5 is a flowchart schematically illustrating steps involved in automatically dynamically adjust a rate at which images are requested, based on the information about a medical device or controller, which is a sub-process of the method of FIG. 4, according to an embodiment of the present invention.

FIG. 5 is a flowchart schematically illustrating sub-operations of operation 408 (FIG. 4), i.e., automatically dynamically adjusting a rate at which images are requested, based on information about a medical device or controller 100. At 500, a table, such as Table 1, is scanned for entries whose names match the information about the medical device controller 100. Recall that information was automatically ascertained from the first OCR text result (operation 406 in FIG. 4), and/or one or more portions, such as a power source icon, of the received image were analyzed to determine information about the medical device controller 100.

At 502, if any matching table entry is found, control passes to 504. In general, entries in Table 1 can be characterized as either increasing the interval above the default or decreasing the interval below the default. In general, table entries that increase the interval value above the default value may be associated with relatively "relaxed" situations, where rapid updates are not needed or not wanted, such as because no pump is connected to a medical device controller 100, or network congestion warrants less frequent updates. On the other hand, table entries that decrease the interval value below the default value may be associated with relatively "tense" situations, where rapid updates are needed, such as because a medical device controller 100 is alarming.

If all the matching table entries increase the interval above the default value, the overall situation may be deemed to be relaxed, and the largest interval value may be selected. In another, more conservative, embodiment, the smallest interval value may be selected.

If all the matching table entries decrease the interval below the default value, the overall situation may be deemed to be tense, and the smallest interval value may be selected, so as to accommodate the most serious issue represented by the matching table entries.

If at least one matching table entry increases the interval above the default value, and at least one matching table entry decreases the interval below the default value, one or more additional rules may be used to determine whether to increase or decrease the interval value. In some embodiments, each table entry has a priority value (not shown), and the matching table entry with the highest priority value is selected. In this way, for example, if some information indicates a short image request interval value is appropriate, but no heart pump is connected to the corresponding medical device controller 100, there is no point in rapidly fetching images from the medical device controller 100, and a long interval value can be selected. This strategy may be implemented as follows.

At 504, of all the matching table entries, the shortest interval value is temporarily stored. Likewise, at 506, of all the matching table entries, the longest interval value is temporarily stored. At 508, either the shortest or the longest interval value is selected from the temporary storage, based on one or more additional rules.

If any matching table entry decreases the interval below the default, then the additional rule may cause the shortest interval value to be selected, or the additional rule may choose a table entry based on priority value or according to other selection criteria. On the other hand, if no matching table entry decreases the interval below the default value, the additional rule may cause the longest interval value to be selected.

At 510, the selected interval value is used to set the image request interval for the medical device controller 100. At 512, information about the next medical device controller is analyzed.

Returning to FIG. 4, at 410, information about the computer network 320 is automatically ascertained. For example, the server 306 may query the computer network 306 or use tools, such as ping, to measure a level of network congestion, utilization and/or available bandwidth. It should be noted that the computer network 320 may include several public and/or private networks, such as wired and/or wireless private networks in a medical institution, public and private wide area networks, such as the Internet, public and private cellular networks, and a private network located within a service provider's facility that houses the server 306. Each of these networks or segments may have its own set of characteristics, and different medical device controllers 100 may be coupled to the server 306 via different networks and segments. Therefore, for each medical device controller 100, or groups of co-located medical device controllers 100, the server 306 may choose to use the characteristics of most restrictive network or segment in a route to that medical device controller 100 or group.

The server 306 may store information indicating to which wide area network, local network and/or network segment, etc. each medical device controller 100 is connected, and/or through which network components or segments computer network traffic travels. This information may be extracted from header information in network packets received by the server 306 from the medical device controllers 100, through use of the traceroute tool or other well-known tools and techniques.

Information about which computer network, segment, etc., to which the various medical device controllers 100 are connected, enables the server 306 to calculate the number of medical device controllers 100 connected to any given computer network, segment, router, etc. This information, together with information about bandwidths of networks and segments between the server 306 and the medical device controllers 100, enables the server 306 to calculate intervals that are sustainable over the available infrastructure. In particular, the server 306 may calculate an aggregate interval that is sustainable over the available infrastructure, and then divide that aggregate interval among the medical device controllers 100, based on information about the individual medical device controllers 100.

The server 306 may store historical information about reliability of computer network connections to various medical device controllers 100 and use relatively shorter intervals on historically unreliable networks. Each medical device controller (MDC) 100 may report the medical institution where the medical device controller 100 is installed. This information may have been entered by a human into a memory of the medical device controller 100, such as through a user interface implemented on the screen 104. The server 306 may use information about which medical institutions host which medical device controllers 100 to predict information, such as network reliability, of newly connected medical device controllers 100.

Examples of the second category of information, i.e., information about the computer network 302, that may be automatically ascertained by the server 306, and how this information influences the image request rate, i.e. triggers and corresponding intervals, are listed in Table 2.

TABLE 2

Exemplary information about a computer network

| Name | Trigger | Interval |
|---|---|---|
| Number of MDCs on same LAN | >10 | 25 sec. |
| Number of MDCs at same institution | >10 | 25 sec. |
| Number of MDCs at same institution | >50 | 40 sec. |
| Number of MDCs at same institution | >100 | 50 sec. |
| Available network bandwidth | <50% | 1 min. |
| History of reliable network connection | Good, ex. >95% | 20 sec. |
| History of reliable network connection | Poor, ex. <75% | 10 sec. |
| Network or segment utilization | >50% | 30 sec. |
| Wi-Fi signal strength at MDC | Stronger than −30 dBm | 20 sec. |
| Wi-Fi signal strength at MDC | Stronger than −67 dBm | 15 sec. |
| Wi-Fi signal strength at MDC | Stronger than −70 dBm | 12 sec. |

TABLE 2-continued

Exemplary information about a computer network

| Name | Trigger | Interval |
|---|---|---|
| Wi-Fi signal strength at MDC | Stronger than −80 dBm | 7 sec. |
| Wi-Fi signal strength at MDC | Weaker than −80 dBm | 3 sec. |

At 412, the rate at which images are requested from the medical device controller 100 is automatically dynamically adjusted, based on the information about the computer network 302, in a manner similar to that discussed with respect to Table 1 and FIG. 5, mutatis mutandis.

Examples of the third category of information, i.e., information about the server 306 or other servers, such as the OCR engine 310, that may be automatically ascertained by the server 306, and how this information influences the image request rate, i.e. triggers and corresponding intervals, are listed in Table 3.

TABLE 3

Exemplary information about servers and server environments

| Name | Trigger | Interval |
|---|---|---|
| Workload on server 306 | <10% CPU busy | 10 sec. |
| Workload on server 306 | <50% CPU busy | 20 sec. |
| Workload on server 306 | >50% CPU busy | 30 sec. |
| OCR invocations on engine 310 | >10 per sec. | 30 sec. |

At 414, the server 306 automatically ascertains information about the server 306 and, optionally, related servers (some not shown), such as the OCR engine 310. At 416, the rate at which images are requested from the medical device controller 100 is automatically dynamically adjusted, based on the information about the server(s), including server 306, in a manner similar to that discussed with respect to Tables 1 and 2 and FIG. 5, mutatis mutandis. Optionally, if a server, such as the server 306 or the OCR engine 310, is found to be busy beyond a predetermined threshold value, such as about 70%, another copy of the server may be spawned, for example using virtual machine technology, and the workload may be divided among the available servers. Conversely, if a server is found to be less busy than a predetermined threshold value, such as about 40%, the server can be terminated, and the terminated server's workload may be distributed among remaining servers.

Examples of the fourth category of information, i.e., information from or about a user of the system 300 or a patient, that may be ascertained by the server 306, and how this information influences the image request rate, i.e. triggers and corresponding intervals, are listed in Table 4. As noted, each monitoring station (MS) 312 displays information about one or more user-selected medical device controllers (MDC) 100. It may be assumed that one user accesses each monitoring station 312. Thus, the number of monitoring stations 312 equals the number of monitoring users.

TABLE 4

Exemplary user inputs and information about users

| Name | Trigger | Interval |
|---|---|---|
| Number of MSs monitoring one MDC | >2 | 15 sec. |
| Number of MSs monitoring one MDC | >4 | 10 sec. |

TABLE 4-continued

Exemplary user inputs and information about users

| Name | Trigger | Interval |
|---|---|---|
| Number of MSs monitoring one MDC | >6 | 5 sec. |
| User input designated a specific MDC | "Important" | 15 sec. |
| User input designated a specific MDC | "Critical" | 10 sec. |
| User input designated a specific MDC | "Monitor" | (user specified) |
| Patient condition | "Critical" | 6 sec. |

Returning to FIG. 4, at 418, an input (command) from a user is received, such as by the server 306, or by one of the monitoring stations 312 and forwarded to the server 306. The user input may, for example, designate a particular medical device controller 100 "Important" or "Critical." Similarly, the user input may designate a particular patient "Critical." A user input ("Monitor") may include a user-specified interval. Each monitoring station 312 may monitor one or more medical device controllers 312. The server 306 may supply information to the monitoring stations 312, as described herein, so the monitoring stations 312 can display this information to their respective users, or the server 306 may be informed by the monitoring stations 312 or by another server (not shown) which monitoring stations 312 are monitoring which medical device controller(s) 100. In any case, the server 306 stores information indicating the number of monitoring stations 312 that are monitoring each medical device controller 100. The server 306 may use this information and/or other information to automatically dynamically adjust the image request rate from individual medical device controllers 100, as indicated at 420 in FIG. 4, in a manner similar to that discussed with respect to Tables 1-3 and FIG. 5, mutatis mutandis.

While the invention is described through the above-described exemplary embodiments, modifications to, and variations of, the illustrated embodiments may be made without departing from the inventive concepts disclosed herein. For example, although specific parameter values, such as interval times and triggers, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. All or a portion of each block, module or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The server 306, or portions thereof, may be implemented by one or more processors executing, or controlled by, instructions stored in a memory. Each processor may be a general purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

What is claimed is:

1. A medical device monitoring system comprising:
a server having one or more processors configured to:
    receive, via a computer network, from at least one medical device controller of a plurality of medical device controllers, at least one image of contents displayed on a screen of the at least one medical device controller;
    send a request to an optical character recognition (OCR) engine to extract textual information from at least a portion of the at least one image;
    receive, from the OCR engine, extracted textual information; and
    send, in response to at least two trigger conditions of a plurality of trigger conditions being met, a request to the at least one medical device controller to change a first rate at which the at least one medical device controller sends images to the server to a second rate, the first and second rates being non-zero,
    wherein the plurality of trigger conditions comprises:
        a first condition based on whether the extracted textual information comprises alarm text;
        a second condition based on whether the extracted textual information comprises an indication that a medical device is connected to the at least one medical device controller; or
        a third condition based on the results of a validation test performed on the extracted textual information,
    wherein each one of the plurality of trigger conditions is specific to at least one of a plurality of predetermined rates at which the at least one medical device controller sends images to the server,
    wherein two or more of the plurality of trigger conditions are specific to different ones of the plurality of predetermined rates, and
    wherein the second rate is selected by the one or more processors in response to a determination that the second rate is the fastest or the slowest of the predetermined rates specific to one or more of the at least two trigger conditions.

2. A method comprising:
receiving, via a computer network, from at least one medical device controller of a plurality of medical device controllers, at least one image of contents displayed on a screen of the at least one medical device controller;
sending a request to an optical character recognition (OCR) engine to extract textual information from at least a portion of the at least one image;
receiving, from the OCR engine, extracted textual information; and
sending, in response to at least two trigger conditions of a plurality of trigger conditions being met, a request to the at least one medical device controller to change a first rate at which the at least one medical device controller sends images to a server to a second rate, the first and second rates being non-zero,
wherein the plurality of trigger conditions comprises:
    a first condition based on whether the extracted textual information comprises alarm text;
    a second condition based on whether the extracted textual information comprises an indication that a medical device is connected to the at least one medical device controller; or
    a third condition based on the results of a validation test performed on the extracted textual information,
wherein each one of the plurality of trigger conditions is specific to at least one of a plurality of predetermined rates at which the at least one medical device controller sends images to the server,
wherein two or more of the plurality of trigger conditions are specific to different ones of the plurality of predetermined rates, and
wherein the second rate is selected in response to a determination that the second rate is the fastest or the slowest of the predetermined rates specific to one or more of the at least two trigger conditions.

3. A non-transitory computer-readable medium encoded with instructions that, when executed by one or more processors, cause the one or more processors to perform a computer-implemented method comprising:
receiving, via a computer network, from at least one medical device controller of a plurality of medical device controllers, at least one image of contents displayed on a screen of the at least one medical device controller;
sending a request to an optical character recognition (OCR) engine to extract textual information from at least a portion of the at least one image;
receiving, from the OCR engine, extracted textual information; and
sending, in response to at least two trigger conditions of a plurality of trigger conditions being met, a request to the at least one medical device controller to change a first rate at which the at least one medical device controller sends images to a server to a second rate, the first and second rates being non-zero,
wherein the plurality of trigger conditions comprises:
    a first condition based on whether the extracted textual information comprises alarm text;
    a second condition based on whether the extracted textual information comprises an indication that a medical device is connected to the at least one medical device controller; or a third condition based on the results of a validation test performed on the extracted textual information,
wherein each one of the plurality of trigger conditions is specific to at least one of a plurality of predetermined rates at which the at least one medical device controller sends images to the server,
wherein two or more of the plurality of trigger conditions are specific to different ones of the plurality of predetermined rates, and
wherein the second rate is selected in response to a determination that the second rate is the fastest or the slowest of the predetermined rates specific to one or more of the at least two trigger conditions.

4. The medical device monitoring system of claim 1, wherein the plurality of trigger conditions comprises the first condition, the second condition, and the third condition, and wherein the first condition, the second condition, and the third condition are specific to different ones of the plurality of predetermined rates.

5. The medical device monitoring system of claim 1, wherein the at least two trigger conditions comprise the first condition.

6. The medical device monitoring system of claim 5, wherein the first condition is a determination that the extracted textual information comprises alarm text, and wherein the second rate is faster than the first rate.

7. The medical device monitoring system of claim 1, wherein the at least two trigger conditions comprise the second condition.

8. The medical device monitoring system of claim 7, wherein the second condition is a determination that the extracted textual information comprises an indication that a medical device is not connected to the at least one medical device controller, and wherein the second rate is slower than the first rate.

9. The medical device monitoring system of claim 1, wherein the at least two trigger conditions comprise the third condition.

10. The medical device monitoring system of claim 9, wherein the third condition is a determination that the validation test failed, and wherein the second rate is faster than the first rate.

11. The medical device monitoring system of claim 10, wherein the validation test checks that the extracted textual information consists of numeric characters or decimal points.

12. The medical device monitoring system of claim 10, wherein the validation test checks that a numeric field is within a predetermined range.

13. The medical device monitoring system of claim 12 further comprising the plurality of medical device controllers, wherein each one of the plurality of medical device controllers is configured to connect to a heart pump.

14. The medical device monitoring system of claim 13, wherein the numeric field is a placement signal value.

15. The medical device monitoring system of claim 13, wherein the numeric field is a motor current value.

16. The medical device monitoring system of claim 13, wherein the numeric field is a blood flow rate.

17. The medical device monitoring system of claim 1 further comprising the plurality of medical device controllers, wherein each one of the plurality of medical device controllers is configured to connect to a heart pump, and wherein the plurality of trigger conditions further comprises:
    a fourth condition based on whether the extracted textual information comprises a placement signal value within a first predetermined range;
    a fifth condition based on whether the extracted textual information comprises a motor current value within a second predetermined range; or
    a sixth condition based on whether the extracted textual information comprises a blood flow rate within a third predetermined range.

18. The medical device monitoring system of claim 17, wherein the plurality of trigger conditions comprises the first condition, the second condition, the third condition, the fourth condition, the fifth condition, and the sixth condition.

19. The medical device monitoring system of claim 1, wherein the second rate is the fastest of the predetermined rates specific to one or more of the at least two trigger conditions, and wherein each one of the predetermined rates specific to one or more of the at least two trigger conditions is faster than the first rate.

20. The medical device monitoring system of claim 19, wherein the fastest of the predetermined rates specific to one or more of the at least two trigger conditions is specific to two or more of the at least two trigger conditions.

21. The medical device monitoring system of claim 1, wherein the second rate is the slowest of the predetermined rates specific to one or more of the at least two trigger conditions, and wherein each one of the predetermined rates specific to one or more of the at least two trigger conditions is slower than the first rate.

22. The medical device monitoring system of claim 8, wherein the second rate is the slowest of the predetermined rates specific to one or more of the at least two trigger conditions.

23. The medical device monitoring system of claim 22, wherein each one of the plurality of trigger conditions is specific to at least one of a plurality of predetermined priority values, and wherein the second condition is specific to a higher predetermined priority value than another one of the at least two trigger conditions.

24. The medical device monitoring system of claim 17, wherein the plurality of trigger conditions comprises the fourth condition, the fifth condition, and the sixth condition, and wherein the fourth condition, the fifth condition, and the sixth condition are specific to different ones of the plurality of predetermined rates.

25. The medical device monitoring system of claim 24, wherein the plurality of trigger conditions comprises the first condition, the second condition, and the third condition, and wherein the first condition, the second condition, and the third condition are specific to different ones of the plurality of predetermined rates.

* * * * *

UNITED STATES PATENT AND TRADEMARK OFFICE
CERTIFICATE OF CORRECTION

PATENT NO. : 12,257,021 B2
APPLICATION NO. : 16/365293
DATED : March 25, 2025
INVENTOR(S) : Alessandro Simone Agnello et al.

It is certified that error appears in the above-identified patent and that said Letters Patent is hereby corrected as shown below:

In the Specification

Column 6, Line 29, Detailed Description of Specific Embodiments:
Now reads: "100."; should read -- 102. --

Column 7, Line 28, Detailed Description of Specific Embodiments:
Now reads: "104"; should read -- 102 --

Column 9, Line 55, Detailed Description of Specific Embodiments:
Now reads: "320"; should read -- 302 --

Column 9, Line 57, Detailed Description of Specific Embodiments:
Now reads: "306"; should read -- 302 --

Column 9, Line 59, Detailed Description of Specific Embodiments:
Now reads: "320"; should read -- 302 --

Column 12, Line 20, Detailed Description of Specific Embodiments:
Now reads: "312."; should read -- 100. --

Signed and Sealed this
Seventeenth Day of June, 2025

Coke Morgan Stewart
*Acting Director of the United States Patent and Trademark Office*